United States Patent
Armstrong

(10) Patent No.: US 9,612,235 B2
(45) Date of Patent: Apr. 4, 2017

(54) HERBICIDAL COMPOUND SCREENING

(71) Applicant: Koch Biological Solutions, LLC, Hayward, CA (US)

(72) Inventor: Joshua I. Armstrong, San Mateo, CA (US)

(73) Assignee: Koch Biological Solutions, LLC, Hayward, CA (US)

( * ) Notice: Subject to any disclaimer, the term of this patent is extended or adjusted under 35 U.S.C. 154(b) by 728 days.

(21) Appl. No.: 13/801,567

(22) Filed: Mar. 13, 2013

(65) Prior Publication Data

US 2013/0267419 A1 Oct. 10, 2013

Related U.S. Application Data

(60) Provisional application No. 61/620,952, filed on Apr. 5, 2012.

(51) Int. Cl.
| | |
|---|---|
| *A01N 25/00* | (2006.01) |
| *C12N 15/82* | (2006.01) |
| *A01H 3/04* | (2006.01) |
| *G01N 33/50* | (2006.01) |

(52) U.S. Cl.
CPC .......... *G01N 33/5097* (2013.01); *A01H 3/04* (2013.01); *A01N 25/00* (2013.01)

(58) Field of Classification Search
CPC ........................... A01N 55/00; G01N 33/5097
See application file for complete search history.

(56) References Cited

U.S. PATENT DOCUMENTS

| | | |
|---|---|---|
| 7,193,129 B2 | 3/2007 | Reuber et al. |
| 7,196,245 B2 | 3/2007 | Jiang et al. |
| 7,238,860 B2 | 7/2007 | Ratcliffe et al. |
| 7,345,217 B2 | 3/2008 | Zhang et al. |
| 7,511,190 B2 | 3/2009 | Creelman et al. |
| 7,598,429 B2 | 10/2009 | Heard et al. |
| 7,601,893 B2 | 10/2009 | Reuber et al. |
| 7,635,800 B2 | 12/2009 | Ratcliffe et al. |
| 7,663,025 B2 | 2/2010 | Heard et al. |
| 7,858,848 B2 | 12/2010 | Reuber et al. |
| 7,956,242 B2 | 6/2011 | Zhang et al. |
| 7,960,612 B2 | 6/2011 | Zhang et al. |
| 8,030,546 B2 | 10/2011 | Reuber et al. |
| 8,110,725 B2 | 2/2012 | Riechmann et al. |
| 8,426,678 B2 | 4/2013 | Riechmann et al. |
| 8,426,685 B2 | 4/2013 | Ratcliffe et al. |
| 2005/0060768 A1 | 3/2005 | Keller et al. |
| 2007/0101454 A1 | 5/2007 | Jiang et al. |
| 2008/0301836 A1 | 12/2008 | Century et al. |
| 2009/0205063 A1 | 8/2009 | Zhang et al. |
| 2009/0265807 A1 | 10/2009 | Kumimoto et al. |
| 2010/0083395 A1 | 4/2010 | Reuber et al. |
| 2010/0083402 A1 | 4/2010 | Heard et al. |
| 2010/0175145 A1 | 7/2010 | Heard et al. |
| 2011/0010792 A1 | 1/2011 | Zhang et al. |
| 2011/0078806 A1 | 3/2011 | Jiang et al. |
| 2011/0119789 A1 | 5/2011 | Creelman et al. |
| 2011/0138499 A1 | 6/2011 | Zhang et al. |
| 2012/0137382 A1 | 5/2012 | Repetti et al. |
| 2012/0144518 A1 | 6/2012 | Sherman et al. |

FOREIGN PATENT DOCUMENTS

| | | | |
|---|---|---|---|
| EP | WO0120020 | * 3/2001 | .......... C07K 14/415 |
| EP | 2465933 A2 | 6/2012 | |
| WO | WO90/08826 A1 | 8/1990 | |
| WO | WO 00/42205 A2 | 7/2000 | |
| WO | WO0120020 A2 | 3/2001 | |
| WO | 03013227 A2 | 2/2003 | |
| WO | 03014327 A2 | 2/2003 | |
| WO | WO 2004/022780 A2 | 3/2004 | |
| WO | 2004031349 A2 | 4/2004 | |
| WO | 2004076638 A2 | 9/2004 | |
| WO | 2005047516 A2 | 5/2005 | |
| WO | 2006130156 A2 | 12/2006 | |
| WO | 2007127186 A2 | 11/2007 | |
| WO | WO 2011/149843 A1 | 12/2011 | |

OTHER PUBLICATIONS

Zhao, Yunde, et al. "SIR1, an upstream component in auxin signaling identified by chemical genetics." Science 301.5636 (2003): 1107-1110.*
Rodriguez-Salus, Melinda Sue, 2012, Dissection of Plant Defense Mechanisms Using Chemical and Molecular Genomics. UC Riverside: Plant Biology. Retrieved from: http://escholarship.org/uc/item/6bx8t6x5.*
Dotson, Stanton B., et al. "A phosphonate monoester hydrolase from Burkholderia caryophilli PG2982 is useful as a conditional lethal gene in plants." The Plant Journal 10.2 (1996): 383-392.*
Tsutsui T, Kato W, Asada Y, Sako K, Sato T, Sonoda Y, Kidokoro S, Yamaguchi-Shinozaki K, Tamaoki M, Arakawa K, Ichikawa T, Nakazawa M, Seki M, Shinozaki K, Matsui M, Ikeda A, Yamaguchi J. DEAR1, a transcriptional repressor of DREB protein that mediates plant defense and freezing stress responses in Arabidopsis. J Plant Res. Nov. 2009;122(6):633-43. doi: 10.1007/s10265-009-0252-6. Epub Jul. 18, 2009.
Wolfgang Lein et al: "Target-based discovery of novel herbicides", Current Opinion in Plant, vol. 7, No. 2, Apr. 1, 2004 (Apr. 1, 2004), pp. 219-255, XP055212449, ISSN: 1369.
H. E. Blackwell: "Chemical Genetic Approaches to Plant Biology Bilogogy" Plant Physiology, vol. 133, No. 2, Sep. 11, 2003 (Sep. 11, 2003), pp. 448-455 XP055212466.
Extended European Search Report, issued 21.09.2015 for Application No. 13772583.4.
Copehneaver, Blaine. International Search Report and Written Opinion for PCT/US2013/34802. Jun. 10, 2013.
Dotson et al., A phosphate monoester hydrolase from Burkholderia caryophilli PG2982 is useful as a conditional lethal gene in plants, The Plant Journal (1996) 10(2), 383-392.

* cited by examiner

*Primary Examiner* — Amjad Abraham
*Assistant Examiner* — Fan Weihua

(57) ABSTRACT

The instant disclosure provides methods to identify herbicidal compositions that consist of a combination of compounds that inhibit the growth of or kill undesired plant species in a synergistic manner. Also provided are herbicidal compositions identified using this method.

7 Claims, 4 Drawing Sheets

HERBICIDAL COMPOUND SCREENING

Figure 1:
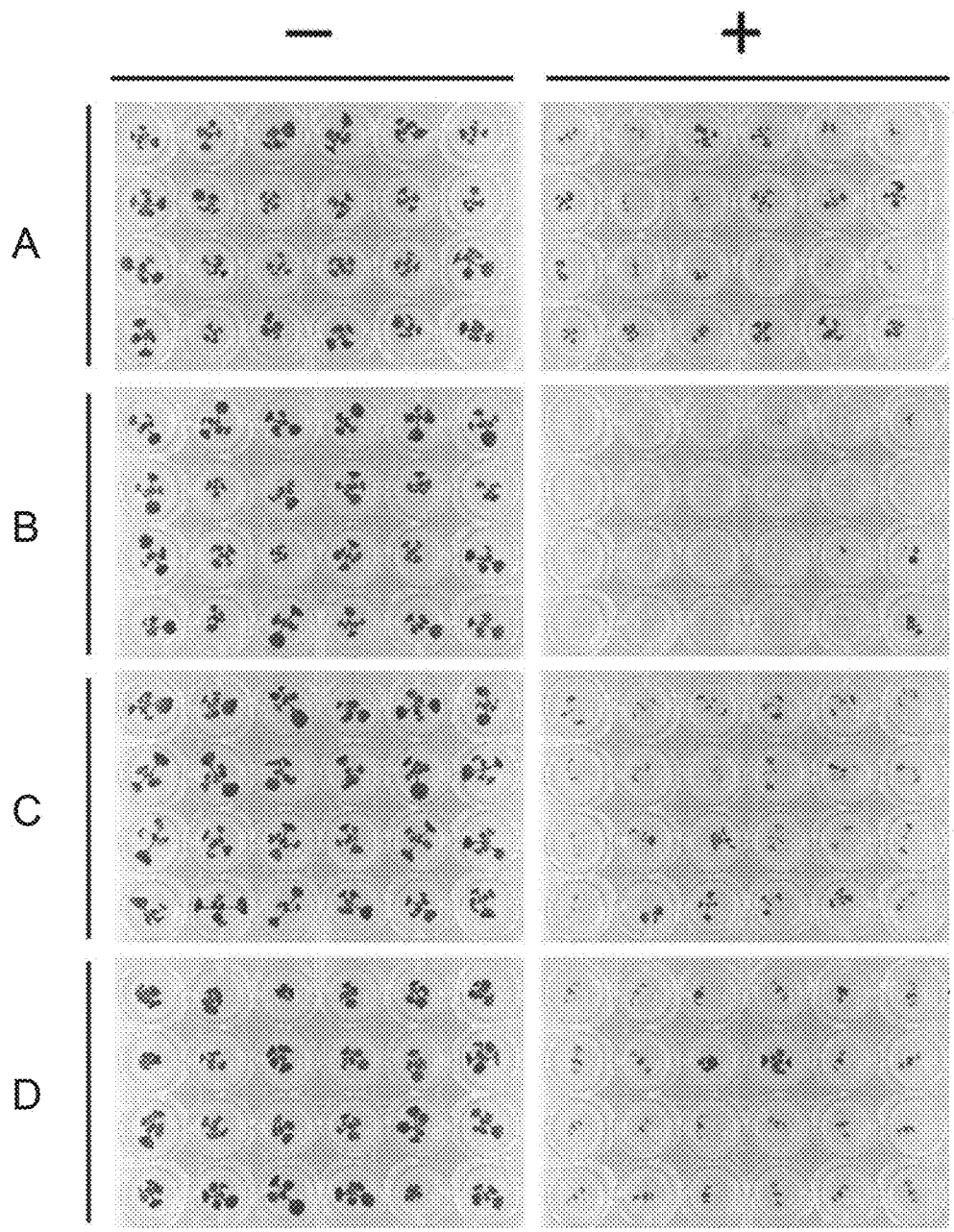

This application claims the benefit of U.S. Provisional Application No. 61/620,952, filed Apr. 5, 2012, the entire contents of which are hereby incorporated by reference.

FIELD OF THE INVENTION

The present disclosure relates to methods of identification of herbicidal compositions.

BACKGROUND

The worldwide herbicide market is large, growing, and spans all continents. The target agricultural species for protection include the major row crops (e.g. corn, soy, and rice) but the dominant application is on cereal plants that are valued at over $3 billion annually. Existing herbicides use various mechanisms to kill plants, such as inhibiting lipid synthesis, inhibiting amino acid synthesis, growth regulation (synthetic auxins), inhibiting photosynthesis, inhibiting nitrogen metabolism, inhibiting pigmentation, disrupting cell membranes, or inhibiting root/seedling growth. The rapid appearance and spread of herbicide-resistant weeds poses a significant challenge. Despite rotating herbicides with different mechanisms of action to reduce the emergence of resistance, it has become increasingly clear from the spread of glyphosate resistance that additional herbicides may be necessary for crop management, and innovative approaches to herbicide discovery are required.

The present disclosure provides a novel approach for the discovery of herbicides with new mechanisms using plant pathways involved in cell death and critical development processes that can be used to identify and prioritize novel herbicidal compounds (and multi-compound formulations).

Examples of how to employ these plant regulatory pathways to identify useful herbicides are provided. Other aspects and embodiments of the instant disclosure are described below and can be derived from the teachings of this disclosure as a whole.

SUMMARY

The present disclosure provides a method for identifying an active herbicidal composition comprising compounds that can potentiate toxic plant regulatory pathways. The compounds in the herbicidal composition synergistically activate the plant regulatory pathways to inhibit the growth of or kill plant cells despite their lack of herbicidal function when acting individually.

The identification of plant regulatory pathways that may be induced to confer toxicity or cell death will facilitate the development of a first screening method for compounds that can potentiate the toxic regulatory pathway. This screening method includes the use of:

(i) a polynucleotide transformed into a plant that encodes an inducible "toxic regulatory polypeptide" that confers toxicity or cell death to the plant when expressed;

(ii) an induction factor exogenously applied to the transformed plant to induce expression of the endogenous toxic regulatory polypeptide to a sub-lethal extent;

(iii) a co-herbicidal compound exogenously applied to the plant that is herbicidal to the transformed plant to which the induction factor has been applied due to the synergistic effects of the co-herbicide and the induced toxic regulatory polypeptide; and (iv) a "potentiating factor", that acts to potentiate the toxic regulatory pathway and causes the expression of an endogenous toxic regulatory polypeptide in a non-transformed plant (for example, a weed plant). This screening method can thus be used to determine effective amounts of the exogenously applied co-herbicidal compound and the potentiating factor to the non-transformed plant that are sufficient to damage or kill the non-transformed plant.

In one aspect of this disclosure, a toxic regulatory polypeptide that is part of plant regulatory pathway that confers toxicity or cell death is identified. A plant line is transformed with a polynucleotide encoding the toxic regulatory polypeptide; in a preferable embodiment, expression of the toxic regulatory polypeptide is regulated by an inducible promoter. Through the use of an experimentally established level of an exogenously applied induction factor, the toxic regulatory polypeptide is expressed in the transformed plant to a sub-lethal level. An example of a suitable induction factor is dexamethasone, as when expression of the regulatory polypeptide is regulated by a dexamethasone-inducible promoter. Said sub-lethal levels of the induction factor may be applied to the transformed plant line or lines in combination with one or more test compounds to identify "co-herbicides" that lack herbicidal activity when applied alone but that are herbicidal when sub-lethal levels of the inducible regulatory polypeptide are expressed in the plant. In a subsequent step of the screening method, co-herbicides can be applied to non-transformed plants, or without the induction factor to the transformed plants, to identify potentiating factors, another class of compounds that act to potentiate the toxic regulatory pathway. Effective amounts of the exogenously applied co-herbicidal compound and the potentiating factor that are sufficient to damage or kill the non-transformed plant may thus be determined with this screening method.

The instant application also pertains to marker genes of the toxic plant regulatory pathways that are identified through genome-wide transcriptional profiling studies based on their ability of being induced following the increase of the activity of the plant regulatory pathway. In an embodiment of the method, the target plant cell and the transgenic plant cell are comprised within a target plant and a transgenic plant, respectively.

The instant application also provides a method of selecting an active herbicidal composition by applying a combination of the compounds that are identified through the reporter system described above to a plant cell and selecting a herbicidal combination consisting of compounds that act synergistically to kill the plant cell.

In another embodiment of the description, a library of compounds was applied to a second plant cell in combination with a first compound identified from the reporter assay system described above. A second compound is selected that kills the second plant cell when applied in combination with the first compound, but does not kill the second plant cell when applied alone. A herbicidal combination is thus identified comprising the first compound and the second compound, which synergistically provide the herbicidal function in the active composition.

The description also provides a method for controlling the growth of a plant by contacting a target plant, or the growth area of the target plant, or a part of the target plant, with a herbicidal quantity of the active composition identified above.

The application additionally provides a method to control the growth of a harmful or unwanted plant in a crop field which comprises the step of applying the herbicidal compound combination identified above at an effective amount to the field.

In some embodiments, the harmful or unwanted plant is a monocot plant.

The description also provides herbicidal compositions comprising a herbicidal quantity of the active composition identified above.

BRIEF DESCRIPTION OF THE SEQUENCE LISTING AND DRAWINGS

The Sequence Listing provides exemplary polynucleotide and polypeptide sequences of this disclosure.

INCORPORATION OF THE SEQUENCE LISTING

The Sequence Listing provides exemplary polynucleotide and polypeptide sequences. The copy of the Sequence Listing, being submitted electronically with this patent application, provided under 37 CFR §1.821-1.825, is a read-only memory computer-readable file in ASCII text format. The Sequence Listing is named "MBI-0140P_ST25.txt", the electronic file of the Sequence Listing was created on Apr. 2, 2012, and is 13,805 bytes in size (14 kilobytes in size as measured in MS-WINDOWS). The Sequence Listing is herein incorporated by reference in its entirety.

FIGS. 1-4 show the deleterious effects of constitutive overexpression of four regulatory proteins in plants. Sequences A and D (SEQ ID NOs: 2 and 8, respectively) are AP2 family transcription factors, Sequence B (SEQ ID NO: 4) is a zinc finger (Z—C2H2) family transcription factor, and Sequence C (SEQ ID NO: 6) is a homeobox (HB) family transcription factor FIG. 1. Twelve or thirteen day-old transgenic seedlings comprised of diverse "toxic" genes (A-D) that have been induced (+) using dexamethasone or mock-treated (−).

Figure 2:
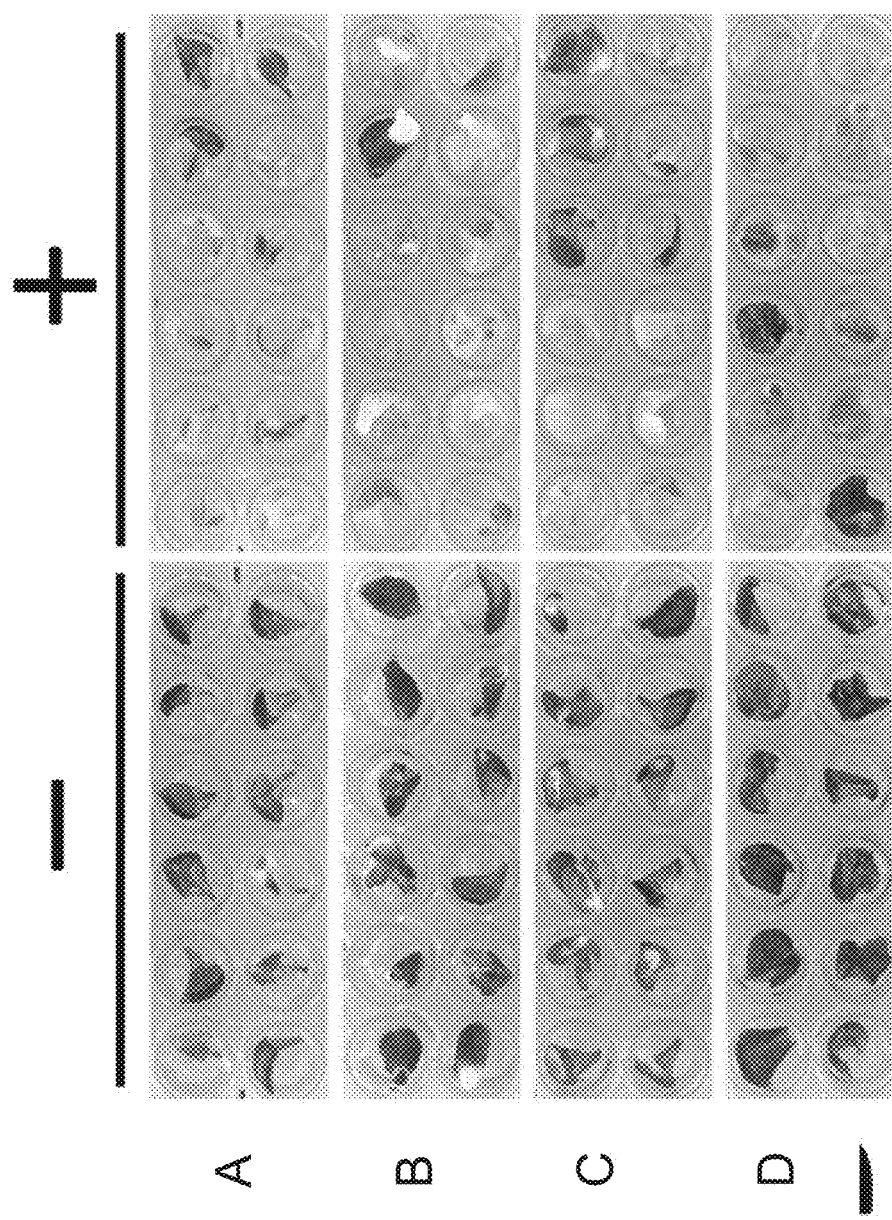

FIG. 2. Leaf-petiole explants from twenty-seven day-old soil-grown transgenic lines (comprised of "toxic" genes A-D) were treated with dexamethasone (+) or mock-treated (−) for seven days to observe the effects of "toxic" gene induction.

Figure 3:
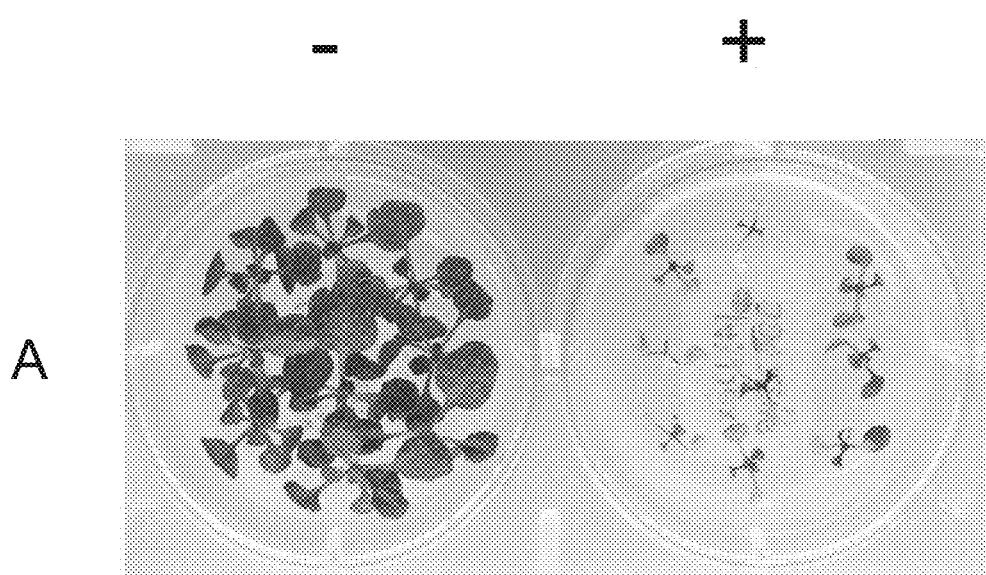

FIG. 3. Fourteen day-old transgenic seedlings (single event, mixture of hemi- and homozygous individuals) after seven days of "toxic" gene A induction (+) compared to the mock-treated, un-induced control seedlings (−).

Figure 4:
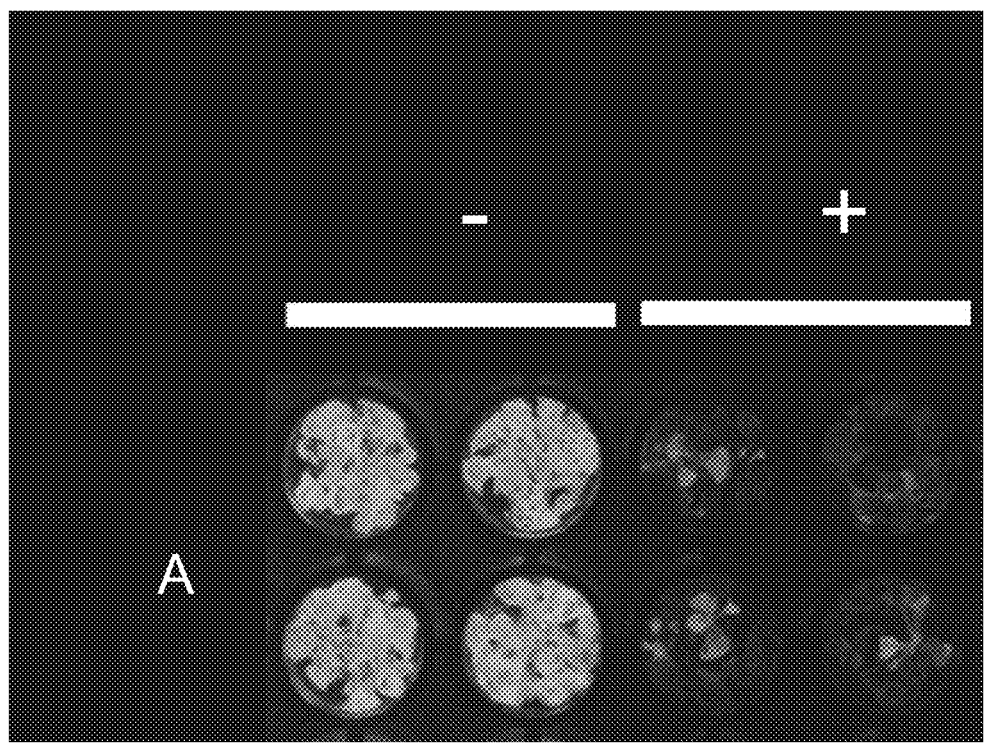

FIG. 4. Nine day-old segregating seedlings (single even, mixture of negative segregant, hemi-, and homozygous individuals) after four days of "toxic" gene A induction (+) compared to the mock-treated, un-induced control seedlings (−). The image is shown in reverse contrast to highlight the living (white) versus necrotic (dark) tissue.

DETAILED DESCRIPTION

The present disclosure generally relates to herbicidally-effective compositions and methods for identifying them. Methods are provided for identification of chemical compounds that can be applied to an organism, for example, a plant or an in vitro culture, to enhance the performance, or modify phenotypes of the organism. Throughout this disclosure, various information sources are referred to and/or are specifically incorporated. The information sources include scientific journal articles, patent documents, textbooks, and World Wide Web browser-inactive page addresses. While the reference to these information sources clearly indicates that they can be used by one of skill in the art, each and every one of the information sources cited herein are specifically incorporated in their entirety, whether or not a specific mention of "incorporation by reference" is noted. The contents and teachings of each and every one of the information sources can be relied on and used to make and use embodiments of this disclosure.

As used herein and in the appended claims, the singular forms "a", "an", and "the" include the plural reference unless the context clearly dictates otherwise. Thus, for example, a reference to "a host cell" includes a plurality of such host cells, and a reference to "a stress" is a reference to one or more stresses and equivalents thereof known to those skilled in the art, and so forth.

DEFINITIONS

"Synergistic" refers to (i) a cooperative effect of a system of multiple components that is greater that a simple additive effect of the individual componentsor (ii) a cooperative effect that produces a result that is not independently obtainable, or obtainable to the same degree by the individual components taken alone. For example, in the present application, many compounds do not inhibit the growth of or kill a plant or plant cell individually, but when they are combined they are able to act synergistically to inhibit the growth of, or kill, a plant or a plant cell.

"Toxic plant regulatory pathway" refers to a plant regulatory pathway that is able to inhibit the growth of or kill a plant when the toxic plant regulatory pathway is induced to a sufficient degree.

"Potentiate toxic plant regulatory pathways" refers to an enhancement of the activation of the toxic plant regulatory pathway.

A "toxic regulatory polypeptide" refers to a plant regulatory polypeptide that can inhibit the growth of, or kill, a plant when the toxic regulatory polypeptide is expressed at a sufficient level. Examples of toxic regulatory polypeptides are provided in the Sequence Listing and include G12 (SEQ ID NO: 2), G2827 (SEQ ID NO: 4, G1540 (SEQ ID NO: 6), and G2298 (SEQ ID NO: 8).

A "toxic gene" refers to a polynucleotide that encodes a toxic regulatory polypeptide.

"Sublethal" refers to a state in which a plant is not killed. In this disclosure, sublethal generally refers to a level of a chemical, compound or composition that is insufficient to cause death of a plant when the chemical, compound or composition is in contact with the plant.

A "sub-lethal dose" refers to a concentration of a chemical or environmental treatment that is applied to a plant or plant cell without causing lethality.

"Herbicidal quantity" refers to a combination of chemical compounds at an amount that can cause plant injury, necrosis, growth inhibition, or death.

"Herbicidal composition" refers to a composition comprising at least one chemical compound that when applied at an effective amount, can cause plant injury, necrosis, growth inhibition, or death.

"Induction factor" with regard to the instant disclosure refers to a compound exogenously applied to a plant, such as a transformed plant, that causes the expression of ("induces") a specific endogenous polypeptide, such as an endogenous toxic regulatory polypeptide. The induction factor may be applied in such a manner that the toxic regulatory polypeptide is expressed in the plant to a sublethal extent. Dexamethasone is an example of an induction factor that may be used to regulate the expression of any polypeptide that is under the regulatory control of a dexamethasone-inducible promoter.

In the instant application, a "co-herbicide" is defined as a compound that lacks or has minimal herbicidal activity when applied alone to a plant, but is more strongly herbicidal when a inducible toxic regulatory polypeptide is expressed in the plant, and the co-herbicide and the toxic regulatory polypeptide act synergistically to produce the stronger herbicidal effect and significantly damage or kill the plant.

A "potentiating factor" refers to a compound that acts to increase the activity of an endogenous toxic regulatory pathway in a plant and causes the expression of an endogenous toxic regulatory polypeptide in the plant. Increasing the activity of an endogenous toxic regulatory polypeptide would be useful for controlling weed or other undesirable plant species.

A "transgenic or transformed plant" refers to a plant which contains a recombinant polynucleotide introduced by transformation. Transformation means introducing a nucleotide sequence in a plant in any manner to cause stable or transient expression of the sequence. This may be achieved by transfection with viral vectors, transformation with plasmids, such as *Agrobacterium*-based vectors, or introduction of naked DNA by electroporation, lipofection, or particle gun acceleration. A transformed plant may refer to a whole plant as well as to seed, plant tissue, plant cells or any other plant material, and to the plant's progeny.

A "vector" is a nucleic acid construct, generated recombinantly or synthetically, comprising nucleic acid elements that can cause expression of a gene. A "donor vector" is a construct for expression of a polynucleotide sequence for a transactivator gene. The transactivator gene is operably linked to a promoter. The promoter region may include tissue active-or-specific promoters, developmental stage active-or-specific promoters, inducible promoters or constitutive promoters.

The term "DNA sequence-specific transactivator" refers to a polypeptide that comprises at least a DNA binding domain that binds to DNA with some degree of specificity and a transcriptional activation domain that has the function of activating transcription. A common feature of some activation domains is that they are designed to form amphiphilic alpha helices with negative charge (Giniger and Ptashne (1987) *Nature* 330:670-672, Gill and Ptashne (1987) *Cell* 51:121-126, Estruch et al (1994) *Nucl. Acids Res.* 22:3983-3989). Examples include the transcription activation region of VP16 or GAL4 (Moore et al. (1998) *Proc. Natl. Acad. Sci. USA* 95: 376-381; and Aoyama et al. (1995) *Plant Cell* 7:1773-1785), peptides derived from bacterial sequences (Ma and Ptashne (1987) *Cell* 51; 113-119) and synthetic peptides (Giniger and Ptashne, supra), or the EDLL domain from plants (PCT publication no. WO2009158591). Exemplary transactivators are those described in Brent and Ptashne, U.S. Pat. No. 4,833,080, herein incorporated by reference, or in Hasselhoff and Hodge, PCT publication no. WO1997030164.

"Activation" of a promoter-reporter construct is considered to be achieved when the activity value relative to control, e.g., a sample that is not treated with a test compound, is 105%, 110%, 120%, 130%, 140%, 150%, 200%, 250%, 300%, 400%, 500%, or 1000-3000% or more higher.

The term "plant" includes whole plants, shoot vegetative organs/structures (for example, leaves, stems and tubers), roots, flowers and floral organs/structures (for example, bracts, sepals, petals, stamens, carpels, anthers and ovules), seed (including embryo, endosperm, and seed coat) and fruit (the mature ovary), plant tissue (for example, vascular tissue, ground tissue, and the like) and cells (for example, guard cells, egg cells, and the like), and progeny of same. The class of plants that can be used in the method of the instant description is generally as broad as the class of higher and lower plants amenable to transformation techniques, including angiosperms (monocotyledonous and dicotyledonous plants), gymnosperms, ferns, horsetails, psilophytes, lycophytes, bryophytes, and multicellular algae.

A "trait" refers to a physiological, morphological, biochemical, or physical characteristic of a plant or particular plant material or cell. In some instances, this characteristic is visible to the human eye, such as seed or plant size, or can be measured by biochemical techniques, such as detecting the protein, starch, or oil content of seed or leaves, or by observation of a metabolic or physiological process, e.g. by measuring tolerance to water deprivation or particular salt or sugar concentrations, or by the observation of the expression level of a gene or genes, e.g., by employing Northern analysis, RT-PCR, microarray gene expression assays, or reporter gene expression systems, or by agricultural observations such as hyperosmotic stress tolerance or yield. Any technique can be used to measure the amount of, comparative level of, or difference in any selected chemical compound or macromolecule in the transgenic plants, however.

"Trait modification" refers to a detectable difference in a characteristic in an organism being treated with the chemical compounds of the instant description relative to a control organism of the same species, the latter including organisms treated with a control compound or a carrier solvent or no treatment. In some cases, the trait modification can be evaluated quantitatively. For example, the trait modification can entail at least about a 2% increase or decrease, or an even greater difference, in an observed trait as compared with a control or wild-type organism. It is known that there can be a natural variation in the modified trait. Therefore, the trait modification observed entails a change of the normal distribution and magnitude of the trait in the plants as compared to control or wild-type organisms.

"Ectopic expression or altered expression or modified expression" in reference to a polynucleotide indicates that the pattern of expression in, e.g., a transgenic organism or tissue, is different from the expression pattern in a wild-type organism or a reference organism of the same species. The pattern of expression may also be compared with a reference expression pattern in a wild-type plant of the same species. For example, the polynucleotide or polypeptide is expressed in a cell or tissue type other than a cell or tissue type in which the sequence is expressed in the wild-type organism, or by expression at a time other than at the time the sequence is expressed in the wild-type plant, or by a response to different inducible agents, such as hormones or environmental signals, or at different expression levels (either higher or lower) compared with those found in a wild-type organism. The term also refers to altered expression patterns that are produced by lowering the levels of expression to below the detection level or completely abolishing expression. The resulting expression pattern can be transient or stable, constitutive or inducible. In reference to a polypeptide, the term "ectopic expression or altered expression" further may relate to altered activity levels resulting from the interactions of the polypeptides with exogenous or endogenous modulators or from interactions with factors or as a result of the chemical modification of the polypeptides.

The term "overexpression" as used herein refers to a greater expression level of a gene in an organism, a cell or a tissue, compared to expression in a wild-type plant, cell or tissue, at any developmental or temporal stage for the gene. Overexpression can occur when, for example, the genes encoding one or more polypeptides are under the control of a strong promoter (e.g., the cauliflower mosaic virus 35S transcription initiation region). Overexpression may also occur under the control of an inducible or tissue specific promoter. Thus, overexpression may occur throughout an organism, in specific tissues of the organism, or in the presence or absence of particular environmental signals, depending on the promoter used.

Overexpression may take place in cells normally lacking expression of polypeptides functionally equivalent or identical to the present polypeptides. Overexpression may also occur in cells where endogenous expression of the present polypeptides or functionally equivalent molecules normally occurs, but such normal expression is at a lower level. Overexpression thus results in a greater than normal production, or "overproduction" of the polypeptide in the organism, cell or tissue.

"Up-regulation" refers to an increase in expression of a gene, a polynucleotide, a gene product (e.g., mRNA or a polypeptide), or the activity of a regulatory pathway of interest in an organism. The term may, for example, refer to the situation where transcription of a specific mRNA is increased, but can also refer to an increase in mRNA or protein levels due to increased stability of the specific mRNA.

"Conditional up-regulation" is an increase in the expression of a gene, a polynucleotide, a gene product, or the activity of a regulatory pathway in response to a particular ex vivo or in vivo signal, e.g., an environmental or cellular condition, contact, or exposure. An inducible promoter or altered RNA stability may be used to conditionally increase gene, polynucleotide, or gene product expression.

"Damage" to a plant refers to an detrimental effect on plant health, and may be caused by a variety of influences, including a treatment that directly or indirectly, alone or in a combination treatment, negatively impacts a plant and adversely affects growth, physiology, quality, and/or fertility. Damage may also refer to a detrimental effect on plant health that can occur across a plant species of interest or to a representative member of a plant species of interest. Damage may manifest in the form of, for example, reduced gamete production or seed count, growth inhibition, reduced biomass, wilting, stunting, chlorosis, promotion of senescence, or necrosis.

DESCRIPTION OF THE SPECIFIC EMBODIMENTS

Toxic Plant Regulatory Pathways

Proprietary screening assays have produced a large number of regulatory proteins that conferred deleterious phenotypes when ectopically and constitutively expressed. These sequences were categorized according to severity of their effects on plants. Exemplary sequences that include conferred deleterious phenotypes when the sequences were ectopically expressed include G12 (SEQ ID NO: 2), G2827 (SEQ ID NO: 4, G1540 (SEQ ID NO: 6), and G2298 (SEQ ID NO: 8) shown in Table 1. Other regulatory protein that confer deleterious phenotypes when ectopically and constitutively expressed may also be envisioned.

TABLE 1

Sequences that conferred deleterious phenotypes when constitutively expressed in plants

| Sequence Identifier | SEQ ID NO: | AGI number | Protein Family | Type: Domain (amino acids from N terminus) |
|---|---|---|---|---|
| G12 | 2 | AT4G36900 | AP2 | AP2: 27-94 |
| G2827 | 4 | AT3G49930 | Z-C2H2 | C2H2-type zinc finger: 96-116, 151-171 |
| G1540 | 6 | AT2G17950 | HB | Homeodomain: 35-98 |
| G2298 | 8 | AT5G21960 | AP2 | AP2: 4-70 |

The presence of each of the domains listed in Table 1 have specific functions that are required for functions of the regulatory protein, including the regulatory proteins listed in Table 1, in which they are found:

AP2 domains are DNA-binding domain found in transcriptional regulators in plants; an example of an AP2 domain is found in EREBP (ethylene responsive element binding protein).

C2H2-type zinc finger domains are nucleic acid-binding protein structures. For C2H2 domains, the first pair of zinc coordinating residues are cysteines, while the second pair are histidines.

Homeodomains are DNA binding domains involved in the transcriptional regulation of key eukaryotic developmental processes. Homeodomains may bind to DNA as monomers or as homo- and/or heterodimers, in a sequence-specific manner.

The Dof domain is a zinc finger DNA-binding domain that shows resemblance to the Cys2 zinc finger.

The AT-hook is a DNA-binding motif. At-hook proteins generally contain at least one AT-hook domain. A second conserved domain, the DUF-296 domain, is associated with AT-hook-containing proteins, which strongly suggests a DNA-binding function for the proteins as a whole.

Many of the regulatory proteins in Table 1 likely play critical roles in cellular fate, homeostasis, and developmental identity and their activity is tightly regulated at both the transcriptional and post-translational level in wild-type plants. When ectopically expressed, the resulting transgenic protein initiates a cascade of gene transcription cycles resulting in the broad array of aberrant morphological and developmental phenotypes. In a few intriguing cases, constitutive expression leads to cell necrosis after approximately one week of growth. In this case, the genes may control apoptosis as part of the hypersensitive defense response.

The ability to activate chemically these cellular necrosis pathways is an attractive herbicide mode-of-action. Those transcription factor pathways that can trigger a toxic phenotype at multiple developmental stages can be prioritized herbicide targets given the opportunity to identify a chemical that results in de-regulation of the target transcription factor activity and similarly induce the deleterious downstream pathways. Many of the observed phenotypes are expected to result from the ectopic expression of the transcription factors during critical early embryo development and induction of expression of the transcription factors at later stages will have few negative consequences. Toxic plant regulatory pathways can be identified where a desirable toxic phenotype are able to be induced at several stages of plant development.

The multi-level regulation of toxic transcription factor proteins may imply the need for multiple compounds to increase the activity of the target pathway and activate the target pathway. Therefore, identification of compounds with synergistic herbicidal activity is of high interest.

Chemical Libraries

Essentially any chemical compound of interest can be tested for its ability to potentiate toxic plant regulator pathways and herbicidal function when it is applied in conjunction with other compounds. Most often, compounds can be dissolved in aqueous or organic (e.g., dimethyl sulfoxide (DMSO)-based) solutions. The assays are designed to screen large chemical libraries and usually include automating the assay steps, which are typically run in parallel (e.g., in microtiter formats on microtiter plates in robotic assays). It will be appreciated that there are many suppliers of chemical compounds, including Sigma-Aldrich® (St. Louis, Mo.), Fluka® Chemika-Biochemica Analytika (Buchs, Switzerland) and the like.

In one preferred embodiment, high throughput screening methods are conducted that provide a combinatorial chemical library containing a large number of test compounds. Such "combinatorial chemical libraries" are screened in one or more assays, as described herein, to identify those library members (particular chemical species or subclasses) that activate or down-regulate the activity of the promoters of the instant description. The compounds thus identified serve as conventional "lead compounds" or can themselves be used as potential or actual agents for treating plants or other organisms.

A combinatorial chemical library is a collection of diverse chemical compounds generated by either chemical synthesis or biological synthesis by combining a number of chemical "building blocks" or reagents. For example, a linear combinatorial chemical library such as a polypeptide library is formed by combining a set of chemical building blocks (amino acids) in numerous iterations for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, small organic molecule libraries (see, e.g., U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; and the like). Other chemistries for generating chemical diversity libraries can also be used. Chemical diversity libraries are also commercially available, e.g., from such companies as 3-Dimensional Pharmaceuticals Inc., Albany Molecular Research Inc., Alchemia Pty. Ltd., Argonaut Technologies Inc., ArQuie Inc, Biofocus DPI, Array Biopharma Inc., Axys Pharmaceutical Inc., Cambridge Combinatorial Ltd., Charybdis Technologies Inc, ChemBridge Corp., CombiChem Inc., ComGenex Inc., Discovery Partners International Inc., Diversa Corp., EnzyMed Inc. Versicor, Gryphon Sciences Inc, Ixsys Inc., Kosan Biosciences Inc., Maxygen Inc., Molecumetics Ltd., Nanoscale Combinatorial Synthesis Inc., Ontogen Corp., Orchid Biocompter Inc., Oxford Asymmetry Ltd., Oxford Molecular Group PLC, Panlabs Inc., Pharmacopeia Inc., Phytera Inc., Proto Gene Inc., Sphere Biosystems Inc., Symyx Technologies Inc., and Systems Integration Drug Discovery Co.

Often, chemical libraries that are screened with the methods of the instant description comprise compounds with molecular weights between 150 and 600, an average cLogP value of 3 (range 0-9), an average number of R-bonding acceptors of 3.5 (range 0-9), an average number of R-bonding donors of one (range 0-4) and an average of three rotatable bonds (range 0-9). Such characteristics are typical of agrichemicals known in the art.

Devices for the preparation of combinatorial libraries are commercially available (see, e.g., 357 MPS, 390 MPS, Advanced Chern Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries, are commercially available (see, e.g., Chembridge, Inc., San Diego, Calif.; ComGenex, Princeton, N.J., Tripos, Inc., St. Louis, Mo., 3D Pharmaceuticals, Exton, Pa., Martek Biosciences, Columbia, Md., etc.) and may be screened with the instant methods.

Reporter Genes

This instant disclosure also provides a reporter assay system that may be used to identify herbicidal compounds that can activate marker genes of a toxic plant regulatory pathway of interest. Expression vectors comprising a promoter or its functional part of a marker gene of the toxic plant regulatory pathway can be used to identify these compounds. Reporters can be any protein that can be used to provide a discernible signal, and include, but are not limited to, fluorescent proteins, such as green or red fluorescent proteins, or variants that produce a fluorescent color; β-glucuronidase (GUS); luciferase; chloramphenicol acetyltransferase; β-galactosidase; and alkaline phosphatase. Commonly used reporter genes include those encoding proteins that can generate quantifiable fluorescent, colorimetric, or luminescent signals. Transcription of the sequences encoding the reporter gene can be determined using any method known in the art. In some embodiments, protein activity of the reporter gene is measured, e.g., using a fluorescent reader or other instrumentation appropriate to the reporter system. Products to assist in determination of reporter activity are commercially available.

Samples that are treated with a test compound, or pool of test compounds, are compared to control samples without the test compound to examine the extent of modulation. Control samples (untreated with activators are assigned a relative activity value. Activation is then achieved when the reporter activity value relative to the control is 105%, 105-150%, optionally 150%, 150-500%, or 500-2000% or more, whereas down-regulation is achieved when the reporter activity value relative to the control is 70-90%, 66%, 20-50%, or 5-10%.

In other embodiments, endpoints other than reporter activity are assayed. For example, expression levels of the mRNA or protein can be measured to assess the effects of a test compound on reporter activation. In this instance, the expression of the reporter construct is measured by assessing the level of mRNA that encodes the reporter gene or the translational fusion of the reporter gene and a polypeptide of interest, or alternatively of the protein product. These assays can be performed using any methods known by those of skill in the art to be suitable. For example, mRNA expression can be detected using amplification-based methodologies, northern or dot blots, nuclease protection and the like. Polypeptide products can be identified using immunoassays.

Introduction of Reporter Constructs into Hosts or Host Cells

Reporter constructs can be introduced into the desired hosts or cells derived there from, such as plants, microbes, mammals, yeast, *Drosophila, C. elegans* by a variety of conventional and well-known techniques. For example, the vector can be introduced directly into the host cells using techniques such as electroporation, microinjection, and biolistic methods, such as particle bombardment.

Microinjection techniques are known in the art and well described in the scientific and patent literature. The introduction of DNA constructs using polyethylene glycol precipitation is described, e.g., in Paszkowski et al. (1984) e *EMBO J.*: 2717-2722. Electroporation techniques are described in Fromm et al. (1985) *Proc. Natl. Acad. Sci.* (USA) 1985 82:5824-5828. Biolistic transformation techniques are described in Klein et al. (1987) Nature, 327: 70-73.

It is envisioned that the transformation methods, identification and increase of the activity of regulatory pathways, and compound treatment methods described herein may be applied to both plants and plant cells. For transforming plants or plant cells, reporter constructs may also be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. *Agrobacterium tumefacien*-mediated transformation techniques, including disarming and use of binary vectors, are well described in the scientific literature. See, for example Horsch et al. (1984) *Science* 223:496-498, and Fraley et al. (1983) *Proc. Natl. Acad. Sci.* (USA) 80:4803-4807. The host plant cells for screening reporter constructs can be from any plant, including both dicots and monocots. Typically, plant cells are from *Nicotiana benthamiana*, or *Arabidopsis thaliana*, or another plant that may be transformed, and preferably is routinely transformed and assayed in the art.

Other plants also can be used in the screening methods taught herein. These include cereals, for example, maize, sorghum, rice, wheat, barley, oats, rye, milo, flax, or gramma grass. Other plant genera include, but are not limited to, *Cucurbita, Rosa, Vitis, Juglans, Gragaria, Lotus, Medicago, Onobrychis; Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Avena, Hordeum, Secale, Allium, Setaria*, and *Triticum*.

Following transformation of the reporter constructs into the plant cell, the transformed cell or plant tissue is selected or screened by conventional techniques. The transformed cell or plant tissue containing the reporter construct can then be regenerated, if desired, by known procedures. Additional methodology for the generation of plants comprising expression constructs for screening chemicals can be found in the art (see, e.g., U.S. Pat. No. 5,614,395).

High Throughput Assays

In high throughput assays, it is possible to screen numerous, for example, several thousand different test compounds in a single day. For example, each well of a microtiter plate can be used to run a separate assay against a selected test compound, or, if concentration or incubation time effects are to be observed, every 5-10 wells can test a single test compound. In addition, pools of test compounds can also be tested where 25 multiple compounds are included in a single test sample. If a 'hit' (a positive result or a result of interest) is identified, the chemicals included in the pool can be individually tested to identify compounds that are able to potentiate toxic plant regulatory pathways. Further, initial hit compounds are subjected to a subsequent high throughput screen to identify a second compound that in combination with the initial hit compound confers plant cell lethality. The ratio and concentration of the two compounds are optimized based on the ability to inhibit or injure the plant or plant cell, and a herbicidal composition comprising the effective combination of the two compounds are then identified.

Treatment of Plants

Once an active herbicidal composition is identified and further validated in accordance with the methods of the instant description, they can be applied to the field to eradicate harmful or unwanted plants.

The selected chemicals can be formulated for treating plants as a liquid or a solid form. For example, in liquid formulations, the plants can be treated with a spray, in a drench application, a drip application, or through irrigation. Formulations are prepared using known methodology and may comprise other reagents conventionally employed in formulation of agricultural chemicals, e.g., emulsifying agents, surfactants, etc. Examples of formulations include emulsifiable concentrates, directly sprayable or dilutable solutions, dilute emulsions, wettable powders, soluble powders, dusts, granules or microcapsules. The methods of application, such as spraying, atomizing, dusting, wetting, scattering or pouring, are selected in accordance with the desired application. For example, a slow-release formulation can be applied as a soil treatment so that a plant is exposed frequently to an isolated chemical (e.g., turf grass). In another example, it may be desirable to incorporate a chemical compound selected in accordance with the method of the instant description into irrigation water for plants that experience frequent droughts (e.g., cotton).

EXAMPLES

The present specification, now being generally described, will be more readily understood by reference to the following examples, which are included merely for purposes of illustration of certain aspects and embodiments of the present disclosure and are not intended to limit the disclosure.

Example I

Identification of Plant Regulatory Pathways that are Capable of Inhibiting the Growth of, or Killing, Plants Two-component transgenic lines were generated to enable a survey of gene-dependent toxicity. The first component comprises a translational fusion of the LexA DNA binding domain, the GAL4 transcriptional activator domain, and the glucocorticoid receptor (GR) that imparts dexamethasone-dependent nuclear localization to the multi-domain synthetic transcriptional activator. This component is expressed constitutively using the CaMV 35S viral promoter and enhancer regulatory sequence. The second component (introduced through transformation) comprises a transcriptional fusion of the opLexA regulatory sequence and the protein-encoding sequence for the target toxic gene candidate. The resulting transgenic lines were subjected to a mock or dexamethasone treatment to evaluate the gene-dependent onset of death and severe morphological defects.

Primary Transformants (T1 Seedling Survey)

Primary transformants of the super-transformed background were selected using marker gene expression (e.g. sulfonamide herbicide resistance). Seeds were surface sterilized and after seven days of growth (continuous 90 µM m-2 s-1, 22°-25° C.) on selection media (80% MS, 1% sucrose, 0.65% PhytoBlend, 0.05% MES, 1.5 mg/L asulam) a panel of at least 48 individuals were transplanted to growth media (50% MS, 0.05% MES, 0.6% PhytoBlend, 0.65 mM potassium dihydrogen phosphate, 0.75 mM magnesium sulfate) containing either dexamethasone (50 µM) or DMSO (mock-treatment). The morphology of the seedlings was evaluated daily for at least one week to prioritize genes regulating highly toxic pathways (FIG. 1). A selection of mock-treated seedlings were subsequently transplanted to soil (Sunshine mix #1) and the plants were grown under continuous light (100-150 µM m-2 s-1, 22°-25° C.) for additional analysis. When the plants were between three and four weeks of age, multiple leaf explants (containing the petiole) were excised from representative plants and soaked in either a dexamethasone (5 µM) or DMSO (mock) aqueous solution. Tissue necrosis was monitored daily for up to one week to further prioritize toxic pathways for subsequent analysis (FIG. 2). Seeds were harvested from individual plants of transgenic lines comprising the recombinant polypeptide encoding the toxic regulatory polypeptide.

Segregating Populations (T2 Seedling Survey)

Seeds of the prioritized T1 lines were surface sterilized and transgenic T2 seedlings were grown on selection media for seven days. A panel of seedlings from each line was subsequently transplanted to growth media containing either dexamethasone (50 μM) or DMSO (mock-treatment). The morphology of the seedlings was evaluated daily for at least one week to prioritize genes regulating highly toxic pathways. A selection of mock-treated seedlings were subsequently transplanted to soil (Sunshine mix #1) and the plants were grown under continuous light (100-150 μM m-2 s-1, 22°-25° C.) and seed stocks were harvested from individual plants of the prioritized lines (FIGS. 3 and 4).

The regulatory proteins listed in Table 1 (supra) were found to confer significant deleterious effects to plants when the proteins were constitutively expressed in those plants.

Example II

Compound Screen Assay Optimization (T3 Homozygous Lines)

Homozygous transgenic lines harboring a recombinant polynucleotide encoding a toxic regulatory polypeptide of interest are selected by evaluating the resistance pattern to the herbicide selection. The selected seed stocks are subsequently surface sterilized and arrayed into the wells of multi-well (typically 96-well) plates at a density of approximately 3-10 seeds per well using a growth media slurry (50% MS, 0.05% MES, 0.5% sucrose, 0.1% PhytoBlend). The seedlings are then germinated and grown under continuous light (90 μM m-2 s-1, 22°-25° C.) for three to six days prior to the addition of dexamethasone (0.1 to 50 μM final concentration). Conditions are identified for each selected line comprised of an inducible toxic gene where the dexamethasone treatment results in induction of the target gene (as assessed by qRT-PCR), but where the induction is insufficient to result in noticeable tissue necrosis, senescence, or growth defects during the course of the assay (1-4 days of subsequent growth).

Example III

Demonstration of Cross-Species Pathway Conservation

Prioritized *Arabidopsis* toxic genes are used to generate transgenic *Setaria* (e.g. *Setaria viridis*) that express high levels of the transgene constitutively or in a gene-induction system. The resulting transgenic lines are surveyed to assess the toxicity of the transgene and the demonstration of cross-species conservation of the herbicidal target pathway. In addition, a phylogenetic analysis is performed to identify the closest ortholog from a selected monocot species (e.g. *Setaria* spp.) The protein-encoding nucleotide sequence is cloned and used to generate transgenic *Setaria* and *Arabidopsis* that express the transgene either constitutively or using a gene-induction system and the resulting transgenic lines evaluated for the toxic effects of the transgene.

Example IV

Hit Compound Identification and Herbicidal Lead Composition Selection

Once optimized conditions (dexamethasone application concentration and timing) are identified according to the methods in Example II, a library of compounds is screened to identify compounds that potentiate the target toxic gene resulting in more rapid tissue necrosis than the control (mock-treated) seedlings. Compound hits are subsequently evaluated for herbicidal effects in the absence of induced toxic gene expression and those with herbicidal effects are de-prioritized in favor of those compounds that require the elevated expression of the toxic gene for herbicidal activity.

Hit compounds are subsequently evaluated for additive or synergistic herbicidal activity. Wild-type seedlings are arrayed in multi-well plates (as described above) and grown for several days prior to the addition of hit compound combinations. Seedling health is evaluated after several additional days of growth to ascertain if specific combinations of hit compounds confer herbicidal activity.

In an alternative approach, a hit compound is selected for a subsequent high-throughput screen of chemicals that could act in conjunction with the hit compound to confer herbicidal activity. As with the initial screen above, only compounds that lack herbicidal activity when applied alone are selected for subsequent evaluation. The combination of the hit compound from the first screen and the hit compound from the second screen is considered a lead composition, and subsequent assays are performed to optimize the relative concentrations of both compounds for herbicidal activity.

Example V

Identifying Marker Genes of the Regulatory Pathway. Hit Compound Identification and Herbicidal Lead Composition Selection Identification of the Marker Genes Transcriptional profiling studies are performed on identified toxic pathways (see Example I) using a proprietary Affymetrix® GeneChip® array or mRNAseq using the Illumina® GA2 platform. In each experiment, samples from multiple time points post-induction are analyzed to identify marker genes that are induced immediately following target gene expression and those that are persistently expressed at high levels relative to mock-treated control plants.

Reporter Assay Development, Characterization and Optimization.

Promoter fragments will be amplified for each marker gene and introduced into a proprietary reporter vector, including (but not limited to) the two-component induction system that leverages the LexA:GAL4 synthetic transcriptional activator complex for subsequence activation of the green fluorescent protein (GFP) reporter gene. The resulting constructs will be used to transform *Arabidopsis* to obtain a panel of independent transgenic lines for subsequent characterization. The reporter systems that generate sufficient signal-to-noise signals are used for a high-throughput chemical screen. Any known induction conditions (from public or proprietary studies) for the marker gene are used to identify lines with a strong up-regulation of reporter signal following promoter activation.

Alternatively, protoplasts from candidate reporter lines are isolated and transfected with the upstream toxic regulatory polypeptide to identify candidate lines for further optimization. Selected lines for each marker reporter system spanning the prioritized toxic TF pathways will be grown for homozygous bulk seed production and subsequent assay optimization experiments in 96-well plates.

Hit Compound Identification and Herbicidal Lead Composition Selection

Once optimal growth and treatment conditions have been identified, a pilot high-throughput screen of a library of chemical compounds are performed on the selected reporter lines. Compounds that induce the reporter gene expression but do not significantly inhibit the growth of or kill the wild type *Arabidopsis* plants are identified.

Hit compounds are subsequently evaluated for additive or synergistic herbicidal activity. Wild-type seedlings are arrayed in multi-well plates (as described above) and grown for several days prior to the addition of hit compound combinations. Seedling health is evaluated after several additional days of growth to ascertain if specific combinations of hit compounds confer herbicidal activity.

In an alternative approach, a hit compound identified from the reporter assay is used in a subsequent high-throughput assay to screen for chemicals that could act in conjunction with the hit compound to confer herbicidal activity. As with the initial screen above, only compounds that lack herbicidal activity when applied alone are selected for subsequent evaluation. The combination of the hit compound from the first screen and the hit compound from the second screen is considered a lead composition, and subsequent assays are performed to optimize the relative concentrations of both compounds for herbicidal activity.

Example VI

Screening of a Chemical Library Using a Screening Assay in a High Throughput Format One μl each of the chemicals from a library purchased from a commercial source (such as ChemBridge™. Inc., San Diego, Calif.) is added to 96 well plates containing in each well 5-10 *Arabidopsis* seeds, which harbor a reporter construct encoding GFP, for instance of the type shown in FIGS. 1-4. The volume of the media in each well is 250 μl and the final concentration of the chemical in each well is 28 μM. The seeds are allowed to germinate and grow in the medium. The data are normalized based on negative controls in the same plate that are not treated with the chemical for one week and the GFP signal is quantified in a 96 well fluorescent reader (TriStar, Berthold, Oak Ridge, Tenn.).

An alternative screening method involves the germination and growth of the *Arabidopsis* seedlings harboring the GFP construct in 96 well plates for 4-7 days prior to the addition of the compound stock solutions. The seedlings are exposed to the compound solution for an additional 1-3 days and the GFP signal quantified in a 96 well fluorescent plate reader (TriStar, Berthold, Oak Ridge, Tenn.).

Example VII

Seed Preparation

Prior to plating, seeds for all experiments are surface sterilized in the following manner: (1) 5 minute incubation with mixing in 70% ethanol; (2) 20 minute incubation with mixing in 30% bleach, 0.01% Triton® X-100; (3) five rinses with sterile water. Seeds are resuspended in 0.1% sterile agarose and stratified at 4° C. for 2-4 days.

Example VIII

Transplant Compound Treatment

Sterile stratified wild-type seeds (100 per plate) are sown on square plates containing the following medium: 80% MS solution, 1% sucrose, 0.05% MES, and 0.65% Phytoblend agar. Plates are incubated at 22° C. under 24-hour light (100 μE m-2 s-1) in a germination growth chamber. On day 8, the seedlings are transferred to 6-well assay plates at a density of 10 seedlings per well. The assay plates contained growth medium spiked with a unique test compound or DMSO (carrier solvent, 0.4% v/v) per well. The compound-treated seedlings are incubated at 22° C. under 24-hour light (100 μE m-2 s-1) in a germination growth chamber.

Example IX

Spray Compound Treatment Procedure

Sterile seeds (50 per plate) are sown on standard Petri dishes containing the following medium: 80% MS solution, 1% sucrose, 0.05% MES, and 0.65% Phytagar. Plates are incubated at 22° C. under 24-hour light (95 μE m-2 s-1) in a germination growth chamber. On day 8, the seedlings are transferred to square growth plates containing fresh medium (15-25 seedlings per plate) and arranged such that their primary roots are exposed and aligned in parallel along the surface of the plate. The plates are sealed with venting tape and returned to the growth chamber, oriented for vertical growth. Typically, on day 9, the plates are sprayed with a 0.01% Spreader Sticker surfactant solution containing the test compound or DMSO (carrier solvent, 0.4% v/v) using a Preval® aerosol sprayer (1.5 mL/plate). The plates are re-sealed and returned to the growth chamber (horizontal orientation) for further analysis.

Example X

Embodiments of the Disclosure

Embodiment 1

The described method comprises identifying a herbicidally-effective composition that damages or kills a cell of a target plant by:

(a) providing a target plant and a control plant of the same plant species;

(b) identifying a toxic regulatory pathway that is capable of damaging or killing the target plant when the activity of the regulatory pathway is increased in the target plant;

(c) conditionally or inducibly increasing the activity of the toxic regulatory pathway to a level that is sub-lethal in the target plant, for example, by transforming the target plant with a polynucleotide that encodes an inducible "toxic regulatory polypeptide" that confers toxicity or cell death to the plant when expressed under the regulatory control of an induction factor;

wherein the target plant is then contacted with the induction factor to a level that is sufficient to increase the activity of the toxic regulatory pathway to an extent that is non-lethal to the target plant;

(d) screening and identifying a co-herbicide that is more damaging or lethal to the target plant than to the control plant (in which the activity of the regulatory pathway has not been increased) when the co-herbicide is contacted with the target and control plants;

(e) identifying a second compound that, (1) when combined with the first compound in an active composition, is capable of damaging or killing the second plant when the second plant is contacted with the active composition; and (2) when contacted with the second plant in a composition lacking the first compound is capable of being less effective at damaging or killing the second plant than the active composition; and (f) identifying an herbicidally effective concentration of the co-herbicide and the potentiating factor that, when exogenously applied to the undesirable plant, the co-herbicide and the potentiating factor act synergistically to damage or kill the undesirable plant.

Embodiment 2

In other aspects of this disclosure, the first plant cell is generated by transforming a target plant cell with a recombinant polynucleotide encoding a toxic regulatory polypeptide which inhibits the growth of, or kills, a plant when expressed at a sufficient level. A sub-lethal dose of a chemical or an environmental treatment is applied to the first plant cell to induce the plant regulatory pathway without killing the plant cell.

Embodiment 3

In another aspect of this disclosure, the first plant cell, the target cell, or the second plant cell is comprised within a first plant, a target plant, or a second plant respectively.

Embodiment 4

In some aspects of the disclosure, a reporter assay system is employed to identify a compound that increases the activity of a toxic plant regulatory pathway. The method steps comprise:

(a) identifying a marker gene polynucleotide of a plant regulatory pathway, wherein the plant regulatory pathway is capable of damaging or killing a target plant cell and the expression of the marker gene is altered when the activity of the regulatory pathway is increased;

(b) introducing an expression cassette comprising a functional part of the promoter region of the marker gene and a reporter gene polynucleotide into a plant to generate a transgenic plant cell;

(c) selecting one or more compounds that alter the expression of the reporter gene polynucleotide in the transgenic plant cell relative to a control compound when contacted with said transgenic plant cell;

(d) applying each of the one or more compound selected in step (c) to a plant cell wherein the activity of the regulatory pathway has been conditionally increased without causing lethality; and (e) selecting a compound that kills the plant cell wherein the activity of the regulatory pathway has been conditionally increased, wherein the compound does not kill a plant cell of the same type and the same species in which the activity of the regulatory pathway is not increased.

The above examples are provided to illustrate the disclosure but not to limit its scope. Although the foregoing disclosure has been described in some detail by way of illustration and example for, purposes of clarity of understanding, it will be obvious that certain changes and modifications may be practiced within the scope of the appended claims. All publications, databases, Genbank sequences, patents, and patent applications cited herein are hereby incorporated by reference to the same extent as if each individual publication or patent application was specifically and individually indicated to be incorporated by reference.

What is claimed is:

1. A method for identifying an herbicidally-effective composition that comprises a first compound and a second compound and confers plant cell lethality, the method comprising:
   a. transforming a first non-transformed plant with a recombinant polynucleotide that comprises an inducible promoter and a toxic regulatory sequence to produce a transformed plant, wherein:
   the toxic regulatory sequence encodes a toxic regulatory polypeptide that is capable of conferring cell death in the transformed plant when the polypeptide is expressed in the transformed plant;
   the toxic regulatory sequence is under regulatory control of the inducible promoter that is activated by an induction factor exogenously applied to the transformed plant, and activation of the toxic regulatory polypeptide in the transformed plant is increased in response to the induction factor; and
   in the absence of activation by the induction factor, the toxic regulatory polypeptide does not kill the transformed plant;
   b. establishing a level of the induction factor exogenously applied to the transformed plant that activates the inducible promoter, wherein the level is sufficient to induce expression of the toxic regulatory polypeptide to an extent that is sub-lethal to the transformed plant;
   c. exogenously applying to the transformed plant a first compound from a pool of test compounds, wherein the first compound lacks herbicidal activity when applied alone to a control plant, to identify a co-herbicidal first compound that is herbicidal to the transformed plant in which a sub-lethal level of the toxic regulatory polypeptide is expressed; and
   d. exogenously applying to a second non-transformed plant the co-herbicidal first compound and a second compound obtained from the pool of test compounds to identify a potentiating factor that acts in combination with the co-herbicidal first compound in the herbicidally-effective composition to confer plant cell lethality in the second non-transformed plant.

2. The method of claim 1, wherein the induction factor is a chemical or environmental treatment applied to the transformed plant.

3. The method of claim 1, wherein the method further comprises step:
   e. determining effective amounts of the exogenously applied co-herbicidal first compound and the potentiating factor applied to the harmful or unwanted plant that are sufficient to confer plant cell lethality.

4. The method of claim 1, wherein the herbicidally-effective composition is applied to a harmful or unwanted plant and application to the harmful or unwanted plant results in cell death in the harmful or unwanted plant or a part thereof.

5. The method of claim 4, wherein the herbicidally-effective composition is applied to a growth area of a harmful or unwanted plant or a part thereof and said application to the growth area kills or retards growth of the harmful or unwanted plant or the part thereof relative to the control plant.

6. The method of claim 4, wherein the harmful or unwanted plant is a monocot plant.

7. The method of claim 4, wherein the harmful or unwanted plant is a dicot plant.

* * * * *

SEQUENCE LISTING

```
<160> NUMBER OF SEQ ID NOS: 8

<210> SEQ ID NO 1
<211> LENGTH: 588
<212> TYPE: DNA
<213> ORGANISM: Arabdiopsis thaliana
<220> FEATURE:
<223> OTHER INFORMATION: G12 (AP2 family)

<400> SEQUENCE: 1
atggagacgg cgactgaagt ggccacggtg gtgtcaactc cggcggttac ggttgcggcg      60
gtggcgacga ggaagagaga taagccgtat aaagggataa ggatgaggaa gtgggggaag     120 tgggtggcg agataagaga gcctaataaa aggtcaagga tctggcttgg ctcttactct      180
actcctgaag cggcggcgcg tgcttacgac acggcggtgt tttatctccg aggtccttct    240
gctcggctta acttcccgga gcttttagcc ggagtgacgg tgacgggagg aggcggagga    300
ggagtgaacg gtggtggaga tatgtcggcg gcgtatataa ggagaaaagc ggcggaggtt    360
ggagcacaag tggatgcgtt agaagcggcg ggggcgggag ggaatcgtca tcatcatcat    420
```

```
catcaacatc aacgtggtaa tcatgattac gtagataatc atagtgatta tcgtattaat    480
gatgatctta tggagtgtag tagtaaagaa gggtttaaga ggtgtaatgg atcgttggaa    540
cgggttgatt taaacaaatt acccgatccg gaaacttcag atgacgat                588
```

```
<210> SEQ ID NO 2
<211> LENGTH: 196
<212> TYPE: PRT
<213> ORGANISM: Arabdiopsis thaliana
<220> FEATURE:
<223> OTHER INFORMATION: G12 polypeptide (AP2 domain in AA coordinates
      27-94)

<400> SEQUENCE: 2
```

```
Met Glu Thr Ala Thr Glu Val Ala Thr Val Val Ser Thr Pro Ala Val
 1               5                  10                  15

Thr Val Ala Ala Val Ala Thr Arg Lys Arg Asp Lys Pro Tyr Lys Gly
             20                  25                  30

Ile Arg Met Arg Lys Trp Gly Lys Trp Val Ala Glu Ile Arg Glu Pro
         35                  40                  45

Asn Lys Arg Ser Arg Ile Trp Leu Gly Ser Tyr Ser Thr Pro Glu Ala
     50                  55                  60

Ala Ala Arg Ala Tyr Asp Thr Ala Val Phe Tyr Leu Arg Gly Pro Ser
 65                  70                  75                  80

Ala Arg Leu Asn Phe Pro Glu Leu Leu Ala Gly Val Thr Val Thr Gly
                 85                  90                  95

Gly Gly Gly Gly Gly Val Asn Gly Gly Gly Asp Met Ser Ala Ala Tyr
            100                 105                 110

Ile Arg Arg Lys Ala Ala Glu Val Gly Ala Gln Val Asp Ala Leu Glu
        115                 120                 125

Ala Ala Gly Ala Gly Gly Asn Arg His His His His Gln His Gln
    130                 135                 140

Arg Gly Asn His Asp Tyr Val Asp Asn His Ser Asp Tyr Arg Ile Asn
145                 150                 155                 160

Asp Asp Leu Met Glu Cys Ser Ser Lys Glu Gly Phe Lys Arg Cys Asn
                165                 170                 175

Gly Ser Leu Glu Arg Val Asp Leu Asn Lys Leu Pro Asp Pro Glu Thr
            180                 185                 190

Ser Asp Asp Asp
        195
```

```
<210> SEQ ID NO 3
<211> LENGTH: 710
<212> TYPE: DNA
<213> ORGANISM: Arabdiopsis thaliana
<220> FEATURE:
<223> OTHER INFORMATION: G2827 (Z-C2H2 family)

<400> SEQUENCE: 3
```

```
ctcaatcatc ttctaatcaa agatcaccac catatggctc tcgacactct caattctccc     60
acctccacca ccacaaccac cgctcctcct cctttcctcc gttgcctcga cgaaaccgag    120
cccgaaaacc tcgaatcatg gaccaaaaga aaacgtacaa aacgtcaccg tatagatcaa    180
ccaaaccctc ctccttctga agaagagtat ctcgctcttt gcctccttat gctcgctcgt    240
ggctcctccg atcatcactc tccaccgtcg gatcatcact ctctttctcc actgtccgat    300
catcagaaag attacaagtg ttccgtctgt ggcaaatctt tcccgtctta ccaagcgtta    360
ggtggacaca aaacaagtca ccggaaaccg gttagtgtcg atgttaataa tagtaacgga    420
```

```
accgttacta ataacggaaa tattagtaac ggtttagttg gtcaaagtgg gaagactcat    480
aactgctcta tatgttttaa gtcgtttccc tctggtcaag cattgggtgg tcacaaacgt    540
tgtcactatg atggtggtaa cggtaacagt aacggtgaca atagccacaa gtttgaccta    600
aatttaccgg ctgatcaagt tagtgatgag acaattggaa aaagtcaact ctccggtgaa    660
gaaacaaagt cggtgttgtg aagaaacaaa gtcggtgttg tgaggaataa                710
```

<210> SEQ ID NO 4
<211> LENGTH: 215
<212> TYPE: PRT
<213> ORGANISM: Arabdiopsis thaliana
<220> FEATURE:
<223> OTHER INFORMATION: G2827 polypeptide (C2H2-type zinc finger domains in aa coordinates 96-116, 151-171)

<400> SEQUENCE: 4

```
Met Ala Leu Asp Thr Leu Asn Ser Pro Thr Ser Thr Thr Thr Thr Thr
 1               5                  10                  15

Ala Pro Pro Pro Phe Leu Arg Cys Leu Asp Glu Thr Glu Pro Glu Asn
            20                  25                  30

Leu Glu Ser Trp Thr Lys Arg Lys Arg Thr Lys Arg His Arg Ile Asp
        35                  40                  45

Gln Pro Asn Pro Pro Ser Glu Glu Glu Tyr Leu Ala Leu Cys Leu
    50                  55                  60

Leu Met Leu Ala Arg Gly Ser Ser Asp His His Ser Pro Pro Ser Asp
65                  70                  75                  80

His His Ser Leu Ser Pro Leu Ser Asp His Gln Lys Asp Tyr Lys Cys
                85                  90                  95

Ser Val Cys Gly Lys Ser Phe Pro Ser Tyr Gln Ala Leu Gly Gly His
                100                 105                 110

Lys Thr Ser His Arg Lys Pro Val Ser Val Asp Val Asn Asn Ser Asn
            115                 120                 125

Gly Thr Val Thr Asn Asn Gly Asn Ile Ser Asn Gly Leu Val Gly Gln
        130                 135                 140

Ser Gly Lys Thr His Asn Cys Ser Ile Cys Phe Lys Ser Phe Pro Ser
145                 150                 155                 160

Gly Gln Ala Leu Gly Gly His Lys Arg Cys His Tyr Asp Gly Gly Asn
                165                 170                 175

Gly Asn Ser Asn Gly Asp Asn Ser His Lys Phe Asp Leu Asn Leu Pro
            180                 185                 190

Ala Asp Gln Val Ser Asp Glu Thr Ile Gly Lys Ser Gln Leu Ser Gly
        195                 200                 205

Glu Glu Thr Lys Ser Val Leu
    210                 215
```

<210> SEQ ID NO 5
<211> LENGTH: 1227
<212> TYPE: DNA
<213> ORGANISM: Arabdiopsis thaliana
<220> FEATURE:
<223> OTHER INFORMATION: G1540 (HB family)

<400> SEQUENCE: 5

```
atctctttac taccagcaag ttgttttctt gctaacttca aacttctctt tctcttgttc     60
ctctctaagt cttgatctta tttaccgtta actttgtgaa caaagtcga atcaaacaca    120 catggagccg ccacagcatc agcatcatca tcatcaagcc gaccaagaaa gcggcaacaa    180
```

-continued

```
caacaacaag tccggctctg gtggttacac cgtgtcgcca accagcacga ggtggacacc    240
gacgacggag caaatcaaaa tcctcaaaga actttactac aacaatgcaa tccggtcacc    300
aacagccgat cagatccaga agatcactgc aaggctgaga cagttcggaa agattgaggg    360
caagaacgtc ttttactggt tccagaacca taaggctcgt gagcgtcaga agaagagatt    420
caacggaaca acatgacca caccatcttc atcacccaac tcggttatga tggcggctaa    480
cgatcattat catcctctac ttcaccatca tcacggtgtt cccatgcaga gacctgctaa    540
ttccgtcaac gttaaactta accaagacca tcatctctat catcataaca agccatatcc    600
cagcttcaat aacgggaatt taaatcatgc aagctcaggt actgaatgtg gtgttgttaa    660
tgcttctaat ggctacatga gtagccatgt ctatggatct atggaacaag actgttctat    720
gaattacaac aacgtaggtg gaggatgggc aaacatggat catcattact catctgcacc    780
ttacaacttc ttcgatagag caaagcctct gtttggtcta gaaggtcatc aagacgaaga    840
agaatgtggt ggcgatgctt atctggaaca tcgacgtacg cttcctctct tccctatgca    900
cggtgaagat cacatcaacg gtggtagtgg tgccatctgg aagtatggcc aatcggaagt    960
tcgcccttgc gcttctcttg agctacgtct gaactagctc ttacgccggt gtcgctcggg   1020
attaaagctc tttcctctct ctctctcttt cgtactcgta tgttcacaac tatgcttcgc   1080
tagtgattaa tgatgcagtt gttatattag tagttaacta gttatctctc gttatgtgta   1140
atttgtaatt actagctaag tatcgtctag gtttaattgt aattgacaac cgtttatctc   1200
tatgatgaat aagttaaatt tatatat                                        1227
```

<210> SEQ ID NO 6
<211> LENGTH: 291
<212> TYPE: PRT
<213> ORGANISM: Arabdiopsis thaliana
<220> FEATURE:
<223> OTHER INFORMATION: G1540 polypeptide (homeodomain in AA
      coordinates 35-98)

<400> SEQUENCE: 6

```
Met Glu Pro Pro Gln His Gln His His His Gln Ala Asp Gln Glu
1               5                   10                  15

Ser Gly Asn Asn Asn Lys Ser Gly Ser Gly Tyr Thr Cys Arg
            20                  25                  30

Gln Thr Ser Thr Arg Trp Thr Pro Thr Thr Glu Gln Ile Lys Ile Leu
        35                  40                  45

Lys Glu Leu Tyr Tyr Asn Asn Ala Ile Arg Ser Pro Thr Ala Asp Gln
    50                  55                  60

Ile Gln Lys Ile Thr Ala Arg Leu Arg Gln Phe Gly Lys Ile Glu Gly
65                  70                  75                  80

Lys Asn Val Phe Tyr Trp Phe Gln Asn His Lys Ala Arg Glu Arg Gln
                85                  90                  95

Lys Lys Arg Phe Asn Gly Thr Asn Met Thr Thr Pro Ser Ser Ser Pro
                100                 105                 110

Asn Ser Val Met Met Ala Ala Asn Asp His Tyr His Pro Leu Leu His
            115                 120                 125

His His His Gly Val Pro Met Gln Arg Pro Ala Asn Ser Val Asn Val
        130                 135                 140

Lys Leu Asn Gln Asp His His Leu Tyr His His Asn Lys Pro Tyr Pro
145                 150                 155                 160

Ser Phe Asn Asn Gly Asn Leu Asn His Ala Ser Ser Gly Thr Glu Cys
                165                 170                 175
```

```
Gly Val Val Asn Ala Ser Asn Gly Tyr Met Ser His Val Tyr Gly
            180                 185                 190
Ser Met Glu Gln Asp Cys Ser Met Asn Tyr Asn Val Gly Gly Gly
            195                 200                 205
Trp Ala Asn Met Asp His His Tyr Ser Ser Ala Pro Tyr Asn Phe Phe
        210                 215                 220
Asp Arg Ala Lys Pro Leu Phe Gly Leu Glu Gly His Gln Asp Glu Glu
225                 230                 235                 240
Glu Cys Gly Gly Asp Ala Tyr Leu Glu His Arg Arg Thr Leu Pro Leu
                245                 250                 255
Phe Pro Met His Gly Glu Asp His Ile Asn Gly Gly Ser Gly Ala Ile
            260                 265                 270
Trp Lys Tyr Gly Gln Ser Glu Val Arg Pro Cys Ala Ser Leu Glu Leu
        275                 280                 285
Arg Leu Asn
    290

<210> SEQ ID NO 7
<211> LENGTH: 1013
<212> TYPE: DNA
<213> ORGANISM: Arabdiopsis thaliana
<220> FEATURE:
<223> OTHER INFORMATION: G2298 (AP2 family)

<400> SEQUENCE: 7
ttttcactat actgtcagct ccaaaacata cctgaataag tgaatataca ttaaaaccta    60
atctatcatc atatccatct ctttccctct ctgcatttag agatatggat gcatccccaa   120
agtacacagg tgtacggaag aggaagtggg gaaaatgggt ggctgagatt cgtctcccca   180
acagccgtga caggatctgg ttaggctctt tcgactctgc tgagaaggcg gcgcgtgctt   240
tcgacgcggc tctttactgt cttcgtggcc ccggagcacg cttcaacttc cccgacaatc   300
ctccggagat tcccggtggt cgttctctga cgccgcagca gattcaggtc gtagctagcc   360
gtttcgcctg cgaggaggag ctactaccac cggaacaaca tcatccgtca ccgccacgtg   420
gcgaccataa taccgaggaa gaagtgataa tttcggcacg tggggaaatt aatagtggta   480
gtggtgggcc tacgttaggg caagttgggg aagataataa caacgagggt aatagtaatg   540
acacgtcgtc gtattggcct ttaatatggg aggaggagaa ttttgtaggt cctcctaact   600
cagatcatga gttcggtttt ttcacagatg attcaaccaa tttgtacttc ccgacacaac   660
aacaacaaca acatcagctc tcgtctgatt tttactatga tggagcttgt gaagatgatt   720
tctctcatta caatattaac ctttggaatt tctgagatcc attttttttgg tgatcttgga   780 ccaaatattc ctatattgat taattcaatt tgtggatttc gaattcgaga tttcaaatga   840
tcttgaacca gaattttcac cacccactag tagtgtgaat catttgtttg aactttgaag   900
cgaatcctat atgccacaat gtaagcaagc tgagtaata gcttcactac ttaattatct    960
tattcttctt cttcttttttg gttattaaaa ccaatctgtt tcatatgatt ttt          1013

<210> SEQ ID NO 8
<211> LENGTH: 216
<212> TYPE: PRT
<213> ORGANISM: Arabdiopsis thaliana
<220> FEATURE:
<223> OTHER INFORMATION: G2298 polypeptide (AP2 domain in AA coordinates
        4-70)
```

```
<400> SEQUENCE: 8

Met Asp Ala Ser Pro Lys Tyr Thr Gly Val Arg Lys Arg Lys Trp Gly
1               5                   10                  15

Lys Trp Val Ala Glu Ile Arg Leu Pro Asn Ser Arg Asp Arg Ile Trp
                20                  25                  30

Leu Gly Ser Phe Asp Ser Ala Glu Lys Ala Ala Arg Ala Phe Asp Ala
            35                  40                  45

Ala Leu Tyr Cys Leu Arg Gly Pro Gly Ala Arg Phe Asn Phe Pro Asp
    50                  55                  60

Asn Pro Pro Glu Ile Pro Gly Gly Arg Ser Leu Thr Pro Gln Gln Ile
65                  70                  75                  80

Gln Val Val Ala Ser Arg Phe Ala Cys Glu Glu Leu Leu Pro Pro
                85                  90                  95

Glu Gln His His Pro Ser Pro Pro Arg Gly Asp His Asn Thr Glu Glu
            100                 105                 110

Glu Val Ile Ile Ser Ala Arg Gly Glu Ile Asn Ser Gly Ser Gly Gly
            115                 120                 125

Pro Thr Leu Gly Gln Val Gly Glu Asp Asn Asn Asn Glu Gly Asn Ser
        130                 135                 140

Asn Asp Thr Ser Ser Tyr Trp Pro Leu Ile Trp Glu Glu Glu Asn Phe
145                 150                 155                 160

Val Gly Pro Pro Asn Ser Asp His Glu Phe Gly Phe Phe Thr Asp Asp
                165                 170                 175

Ser Thr Asn Leu Tyr Phe Pro Thr Gln Gln Gln Gln Gln His Gln Leu
            180                 185                 190

Ser Ser Asp Phe Tyr Tyr Asp Gly Ala Cys Glu Asp Asp Phe Ser His
        195                 200                 205

Tyr Asn Ile Asn Leu Trp Asn Phe
210                 215
```